(12) United States Patent
Ahlen

(10) Patent No.: US 10,254,234 B2
(45) Date of Patent: Apr. 9, 2019

(54) ARRANGEMENT AND METHOD FOR PRODUCT CONTROL

(71) Applicant: Optonova Sweden AB, Solna (SE)

(72) Inventor: Hans Ahlen, Stockholm (SE)

(73) Assignee: Optonova Sweden AB, Solna (SE)

( * ) Notice: Subject to any disclaimer, the term of this patent is extended or adjusted under 35 U.S.C. 154(b) by 153 days.

(21) Appl. No.: 15/301,594

(22) PCT Filed: Mar. 31, 2015

(86) PCT No.: PCT/SE2015/050403
§ 371 (c)(1),
(2) Date: Oct. 3, 2016

(87) PCT Pub. No.: WO2015/156725
PCT Pub. Date: Oct. 15, 2015

(65) Prior Publication Data
US 2017/0023490 A1    Jan. 26, 2017

(30) Foreign Application Priority Data
Apr. 7, 2014  (SE) ...................................... 1450427

(51) Int. Cl.
*G01N 21/898* (2006.01)
*G01B 11/24* (2006.01)
(Continued)

(52) U.S. Cl.
CPC ............ *G01N 21/898* (2013.01); *B65G 13/07* (2013.01); *G01B 11/002* (2013.01); *G01B 11/14* (2013.01);
(Continued)

(58) Field of Classification Search
CPC ............ G01N 21/8901; G01N 21/8986; G06T 7/0004; H04N 5/247; H04N 5/2256; G01B 11/14; G01B 11/002; G01B 11/24
(Continued)

(56) References Cited

U.S. PATENT DOCUMENTS 4,647,208 A    3/1987  Bieman
4,891,530 A    1/1990  Hatji
(Continued)

FOREIGN PATENT DOCUMENTS

EP    2634565 A1    9/2013
WO    WO 2000/070360 A1    11/2000

OTHER PUBLICATIONS

International Searching Authority, International Search Report and Written Opinion for Application No. PCT/SE2015/050403, dated Jul. 16, 2015, 9 pages, The Netherlands.
(Continued)

*Primary Examiner* — Thai Q Tran
*Assistant Examiner* — Jose M Mesa
(74) *Attorney, Agent, or Firm* — Alston & Bird LLP

(57) ABSTRACT

The invention relates to an arrangement for product control of a product (20, 21), during or after a production process, at a transport arrangement (10, 11) which is arranged to transport the product (20, 21) to be controlled. The arrangement comprises a first camera arrangement (31) which is arranged to take at least one image of at least a part of the product (20, 21) when the product is in or at the transport arrangement (10, 11). The arrangement also comprises a first illumination arrangement (30; 60) which is arranged to emit light for detection by the first camera arrangement (31). The arrangement also comprises a computation unit which is arranged to receive said at least one image from the first camera arrangement (31) and to determine at least one
(Continued)

geometrical property of the product (20, 21) based on said at least one image. The invention also relates to a method, a computer program and a computer program product for controlling a product which is transported during or after the production process.

26 Claims, 5 Drawing Sheets

(51) Int. Cl.
| | |
|---|---|
| *B65G 13/07* | (2006.01) |
| *G01B 11/14* | (2006.01) |
| *H04N 5/247* | (2006.01) |
| *G01B 11/00* | (2006.01) |
| *G01B 11/25* | (2006.01) |
| *G01N 21/89* | (2006.01) |
| *G06T 7/00* | (2017.01) |
| *H04N 5/225* | (2006.01) |

(52) U.S. Cl.
CPC .......... *G01B 11/24* (2013.01); *G01B 11/2513* (2013.01); *G01N 21/8901* (2013.01); *G01N 21/8986* (2013.01); *G06T 7/0004* (2013.01); *H04N 5/2256* (2013.01); *H04N 5/247* (2013.01); *G01N 2201/06113* (2013.01)

(58) Field of Classification Search
USPC .......................................................... 348/92
See application file for complete search history.

(56) References Cited

U.S. PATENT DOCUMENTS

| | | | |
|---|---|---|---|
| 8,706,572 B1* | 4/2014 | Varadarajan | G06Q 30/00 |
| | | | 705/27.2 |
| 2002/0024677 A1 | 2/2002 | Metcalfe et al. | |
| 2008/0161947 A1* | 7/2008 | Niedermeier | G01N 21/9027 |
| | | | 700/90 |
| 2011/0181873 A1* | 7/2011 | Yavets-Chen | G01N 21/55 |
| | | | 356/237.2 |
| 2012/0268585 A1* | 10/2012 | Markwort | G01N 21/9501 |
| | | | 348/87 |
| 2018/0011477 A1* | 1/2018 | Barlier | G05B 19/4099 |

OTHER PUBLICATIONS

Swedish Patent and Registration Office, Office Action for Application No. 1450427-8, dated Nov. 21, 2014, 9 pages, Sweden.

\* cited by examiner

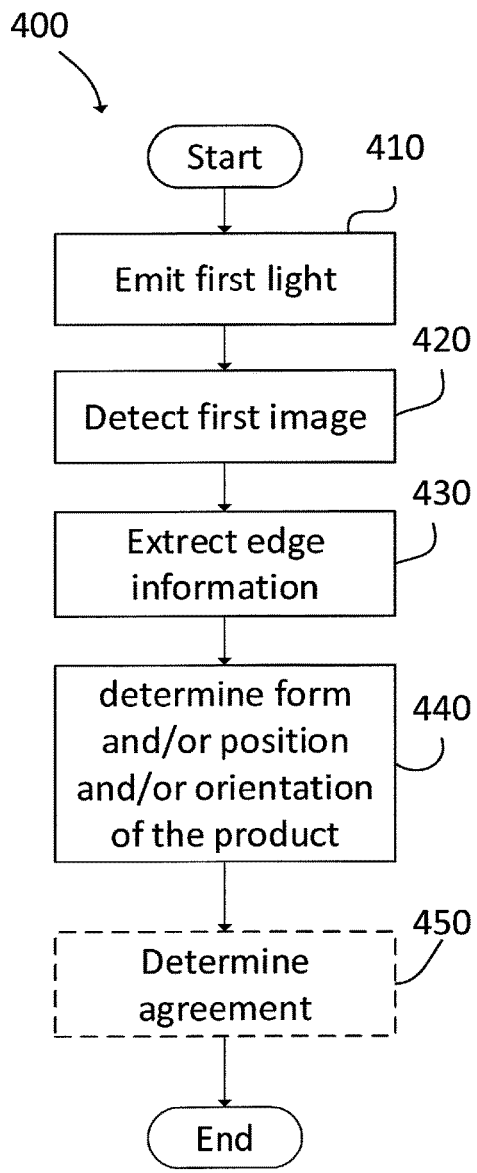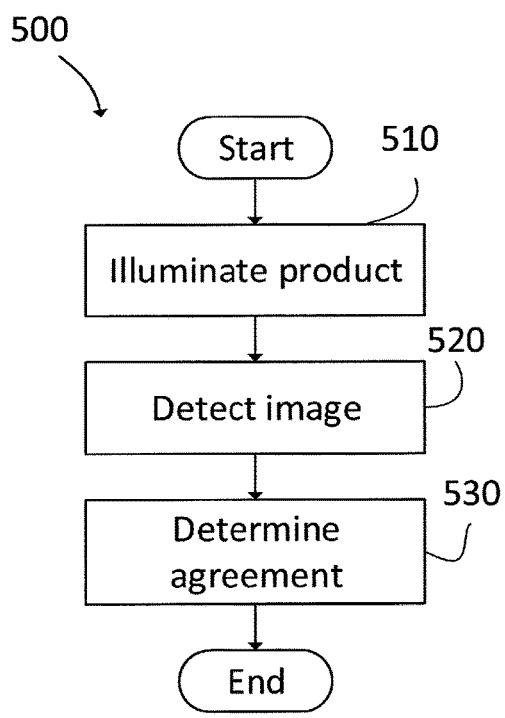
Fig. 4
Fig. 5

ARRANGEMENT AND METHOD FOR PRODUCT CONTROL

CROSS REFERENCE TO RELATED APPLICATIONS

This application is a National Stage Application, filed under 35 U.S.C. § 371, of International Application No. PCT/SE2015/050403, filed Mar. 31, 2015, which claims priority to Swedish Application No. 1450427-8, filed Apr. 7, 2014; the contents of both which as are hereby incorporated by reference in their entirety.

BACKGROUND

Related Field

The present invention relates to an arrangement, a method, a computer program and a computer program product for product control.

Description of Related Art

The production of flat pack furniture gets more and more automated. Less people should produce more and more furniture without renouncing quality of what should be produced. The production lines get more and more complex and the investment costs for new production lines are rising. It is thus important to keep high availability at each production line and to shorten adjusting times between product changes. A time-demanding moment when changing the product is to manually control holes and dimensions of the first pieces and to adjust the production arrangement so that the panels are in agreement with a specification before the new panel type can be produced. The production capacity of the production lines is thus limited.

Important quality measures of flat pack furniture panels are that all holes exist at the correct position, have the correct size and the correct depth. In case errors exist at the holes, it is risked that the end users complain about the furniture. Further, the size (for example length, width and rectangularness) and the form should be correct. Today this part of quality control is basically performed manually via taking random samples of panels which are controlled manually or semi-manually at separate measuring tables. Since the production speed is high a lot of furniture with errors can have been produced between the random samples, and these furniture have to be corrected, or, which is more common, discarded. Further, it is not uncommon that panels with functional errors, such as with some missing hole, reach the end users.

Beside the above named quality measures the aesthetics of the surface of the panels should be without any disturbing defects.

Above named problems relate not only to the production of flat pack furniture, but also to the production of other products.

BRIEF SUMMARY

An object of the present invention is to reduce the disadvantages of the above described arrangements and methods for product control.

A further object of the present invention is to present an arrangement, a method, a computer program, and a computer program product for fast product control.

Yet a further object of the present invention is to present an arrangement, a method, a computer program and a computer program product for space-saving product control.

Yet a further object of the present invention is to present an arrangement, a method, a computer program, and a computer program product for accurate product control.

At least some of the objects are achieved by an arrangement for product control of a product, during or after a production process, at a transport arrangement which is arranged to transport the product to be controlled. The arrangement comprises a first camera arrangement which is arranged to take at least one image of at least a part of the product when the product is in or at the transport arrangement. The arrangement also comprises a first illumination arrangement. The first illumination arrangement is arranged to emit light for detection by the first camera arrangement. The arrangement further comprises a computation unit which is arranged to receive said at least one image from the first camera arrangement. The computation unit is further arranged to determine at least one geometrical property of the product based on said at least one image.

Through this arrangement the possibility is provided to perform product controls in a space-saving manner. No further components are needed on or in the transport arrangement. As an example, no orientation or fastening elements are needed on or in the transport arrangement which put the product into a specific condition and/or a specific position compared to the first camera arrangement. In such a way, transport arrangements in existing production lines can be used without the need of a bigger space for a rearrangement of the transport arrangement.

The product can, for example, preferably be controlled before it is wrapped or packed up. Further, the arrangement accomplishes a very fast result of the product control so that systematic production errors can be found fast. By this the production can be stopped fast at potential errors and/or these errors can be fixed fast.

In one embodiment the arrangement is arranged in such a way that the biggest part of the light from said first illumination arrangement which arrives at said first camera arrangement, arrives at said first camera arrangement by way of the light being sent there from a side of the product which is opposite the side of the product where the first camera arrangement is situated.

By that the image of the product is basically dark, whereas the light which reaches the camera is basically not reflected from the product. By this the edges of the product appear very distinct in the image. Especially in case the product has rounded edges this embodiment facilitates to see the edges of the product much more distinct compared to other arrangements.

In one embodiment the first illumination arrangement is situated at the same side of the product as the first camera arrangement. The first illumination arrangement is preferably arranged in relation to the first camera arrangement in such a way that the angle of incidence from the illumination is the same or nearly the same as the angle of observation for the first camera arrangement for each point in the image plane of the camera arrangement. The arrangement further comprises a retro-reflective element which is arranged at an opposite side of the product in relation to the side of the first camera arrangement and the first illumination arrangement. Said retro-reflective element is further arranged to reflect at least a part of the light which is sent from the first illumination arrangement to the first camera arrangement.

By that arrangement the first camera arrangement and the first illumination arrangement can be situated at the same or nearly the same position. This reduces the needed space for potential cables or support arrangements. By that an especially space-saving arrangement can be achieved. Further, a retro-reflective element facilitates sharp contrasts in the image between the product and the background, which facilitates the determination of at least one geometrical property of the product.

In a further embodiment at least one calibration object is arranged in the field of view of the first camera arrangement. Said at least one calibration object is preferably partly retro-reflective and is arranged in such a way that the light arriving from the first illumination arrangement is reflected from said at least one calibration object to the first camera arrangement.

By that the calibration of the first camera arrangement is facilitated, or the accuracy of the calibration is increased, respectively. By that a more accurate determination of said at least one geometric property of the product is achieved.

In yet another embodiment the transport arrangement comprises a roller conveyor.

This facilitates a fast and easy transport of the product.

In yet another embodiment the first illumination arrangement is arranged on the side opposite to the first camera arrangement. The first illumination arrangement preferably comprises a luminous screen.

With the help of a luminous screen a high and even light emission can be achieved.

In yet another embodiment the computation unit is further arranged to determine the location of the edges of the product in said at least one image and thereby the position and/or orientation of the product on or in the transport arrangement.

By that a relative coordinate system can be attributed to the product in a quite simple way, wherein a reference point of the relative coordinate system, for example the origin, always will be situated at a specific point of the product and wherein the orientation of the relative coordinate system will follow the orientation of the product.

In yet another embodiment said at least one geometric property comprises at least a part of the outer contours of the product.

By that an especially advantageous way of determining the position and/or orientation of the product is achieved.

In yet another embodiment the computation unit is arranged to calculate at least some of the width, length, rectangularness, or form of the product.

This facilitates an easy comparison with the specification of the product.

In yet another embodiment the first illumination arrangement comprises light emitting diodes, which preferably emit pulsed light.

This minimises power consumption, while at the same time the pulsing prolongs the life time of the light emitting diodes, and the heat generation of the light emitting diodes. Thereby the heating of the first camera arrangement is also minimised in case the first camera arrangement is situated at the same or nearly the same position as the first illumination arrangement.

In yet another embodiment the product which is to be controlled is a flat or basically flat object. The flat or basically flat object is preferably a panel.

Thereby the invention is especially suitable in the furniture industry, where many products or at least parts of products are flat or basically flat.

In yet another embodiment the arrangement comprises at least one second illumination arrangement. Said second illumination arrangement is arranged in relation to the transport arrangement in such a way that light from said at least one second illumination arrangement is reflected from the product to the first camera arrangement. The computation unit further is arranged to determine a groove and hole configuration of the product on the side which is faced to the first camera arrangement based on said at least one image. The groove and hole configuration preferably comprises the presence of potential holes and potential grooves, and/or the position of potential holes and potential grooves in relation to the product and/or the size of potential holes and potential grooves.

By that an important controlling function is added to the product control. The presence and/or position and/or size of potential holes and/or grooves is often crucial for the functioning of the product.

In yet another embodiment the taking of the image by the first camera arrangement is done when both said first illumination arrangement and said at least one second illumination arrangement illuminate the product simultaneously.

By that it is assured that at least one geometrical property and said potential hole and/or groove configuration are on the same image and thereby in the same coordinate system. Therefore, no relative error between said at least one geometrical property and said potential hole and/or groove configuration occurs.

In yet another embodiment at least said second illumination arrangement emits stroboscopic light.

This facilitates a sharp image of the product event if it is moving fast on the conveyor belt.

In yet another embodiment the arrangement further comprises a second camera arrangement. The second camera arrangement is arranged to take at least one image of at least a part of the product while the product is situated in or on the transport arrangement. The arrangement further comprises a third illumination arrangement which is arranged in relation to the transport arrangement in such a way that the light of said third illumination arrangement is reflected from the product to the second camera arrangement. The second camera arrangement is then situated on the side of the product which is opposite to the first camera arrangement. The computation unit is further arranged to receive at least one image of the second camera arrangement and to determine the groove and hole configuration of the product on the side which is faced to the second camera arrangement based on said at least one image from the second camera arrangement.

This facilitates detecting the hole and/or groove configuration from more than one side.

In yet another embodiment the taking of the image of the second camera arrangement is synchronised in time with the taking of the image of the first camera arrangement. Preferably at least one second calibration object with a fixed relation to said first calibration object is arranged in the field of view of the second camera arrangement.

By that, information which is achieved from an image taken from the first camera arrangement can be used to increase the accuracy when values are determined based on an image from the second camera arrangement. If at least one second calibration object is in the field of view of the second camera arrangement, and if said at least one calibration object is in a fixed relation to said at least one calibration object, no bigger demands have to be put regarding the accuracy and the robustness of the fastening of the second camera arrangement. With the help of the fixed relationship between the calibration objects, images from the first and the second camera arrangement, respectively, can be spatially related to each other even if one or both camera arrangements are exposed for vibrations or other impacts which can cause a changing of the direction of the field of view.

In yet another embodiment at least one calibration object is arranged in the field of view of the second camera arrangement.

This further increases the accuracy and the calibration accuracy.

In yet another embodiment the first illumination arrangement and the potential other illumination arrangement are arranged to emit light at a first wavelength or at a first wavelength range. The third illumination arrangement is arranged to emit light at a second wavelength or at a second wavelength range. The second wavelength or the second wavelength range is different from the first wavelength or the first wavelength range, respectively. The first camera arrangement is then arranged to detect light essentially outside the second wavelength or the second wavelength range. The second camera arrangement is arranged to detect light essentially outside the first wavelength or the first wavelength range.

Thereby the amount of unwanted scattered light in the camera arrangements is minimised.

In yet another embodiment the arrangement further comprises a first laser arrangement which is arranged to project at least a first laser line on the product basically crosswise to the transport direction of the transport arrangement. This is done in such a way that said first laser line at least partially is in the field of view of the first camera arrangement. The first laser arrangement is further arranged to form an imagined triangle between said first laser arrangement, said first camera arrangement and the product. Preferably no distance in the imagined triangle is substantially longer or shorter than another distance in the imagined triangle. The computation unit is further arranged to compute a distance between the product and the first camera arrangement based on triangulation with the help of the known distance between the first camera arrangement and the first laser arrangement, the pointing direction of the first laser arrangement, and the placing of the first laser line on said received at least one image.

By that, the computation unit can compensate for movements of the product in the direction of the first and/or the second camera arrangement, or for rotations of the product which imply a distance change for at least a part of the product in relation to a camera arrangement. In such a way the accuracy of the product control is increased further.

In yet another embodiment the arrangement further comprises a second laser arrangement which is arranged to project a second laser line on the product basically crosswise to the transporting direction of the transport arrangement. This is done in such a way that the second laser line is at least partially in the field of view of the first camera arrangement. The second laser arrangement is further arranged to form an imagined triangle between the second laser arrangement, the first camera arrangement, and the product. The distance between the second laser arrangement and the first camera arrangement in the imagined triangle is preferably substantially shorter than the two other distances in the imagined triangle. The computation unit is further arranged to compute a distance between the product and the first camera arrangement at many points along the second laser line based on triangulation with the help of the known distance between the first camera arrangement and the second laser arrangement, the pointing direction of the second laser arrangement and the placing of the second laser line on said received at least one image. The computation unit is further arranged to determine the depth of potential holes or grooves based on the computed distance between the product and the first camera arrangement at many points.

Thereby further control of the product is facilitated.

In yet another embodiment, when the arrangement comprises said at least one additional illumination arrangement, the computation unit is further arranged to identify damages on the surface of the product based on said at least one image.

Thereby further control of the product is facilitated.

By yet another embodiment according to claim 17 it is facilitated to determine whether the product has been bent and/or turned and in that case how much. Such bendings/windings appear, for example, if the moisture from products made of solid wood evaporates with different speeds at different sections. It is important to determine whether a potential bending is so big that the product no longer can be sent to the customer, for example since the appearance of the product has been changed too much due to the bending, or since the bending affects the functioning of the product. Further it is facilitated to determine the position of the product in relation to the transport arrangement. In such a way a potential "bounding" or bouncing on the transport arrangement is determined and other computations can take this into account. Consideration can, for example, be taken to the bounding or bouncing when determining a geometrical property of the product.

At least one of the objects is also achieved with the help of a method for controlling a product which is transported with the help of a transport arrangement during or after the production process. The method comprises emitting first light to the product from at least a first side in such a way that a part of the first light reaches the product and the other part of the first light basically is retro-reflected from a surface which is situated on the opposite side of the product. The method also comprises detecting a first image of the product on basically the same side of the product from which the first light is emitted in such a way that the angle of incidence from the illumination is the same or basically the same as the angle of observation for each point in the image plane. The method further comprises extracting edge information from the first detected image and determining the form and/or position and/or orientation of the product in the image based on the extracted edge information.

By that it is facilitated to perform a determination of the form and/or position and/or orientation in a space-saving matter. At the same time the determination of the form and/or position and/or orientation of the product is simplified due to increased contrast in the image.

In one example the method further comprises determining whether the geometry of the product is in agreement with a pre-defined specification of the product based on the determined form and/or position and/or orientation.

By that a space-saving and accurate method for product control is facilitated. Further, the method facilitates to get a result from the product control very fast, leading to the fact that production errors can be found fast. By that the production can be stopped fast at potential errors and/or these errors can be fixed fast.

In yet another example the geometry of the product comprises at least some of the width, length, rectangularness, and/or other two-dimensional geometrical form of the product. This facilitates to compare the product easily with a specification.

In yet another example the method further comprises additionally illuminating the product from one or several angles which preferably don't differ with more than 90 degrees from the direction from which the first light is emitted. The method further comprises detecting in an image, which preferably is the first image, the light from the additional illumination which has been reflected there from the product. The method further comprises determining whether the hole and/or groove configuration of the product is in agreement with a specification of the product based on the detected image.

This facilitates further control of the product.

In yet another example the hole and/or groove configuration of the product comprises at least some out of presence, position, or size of the holes and/or grooves.

This facilitates determining often crucial properties for the functioning of a product.

In yet another example the method further comprises projecting at least one laser line basically crosswise to the moving direction of the product. The method further comprises detecting said projected at least one laser line in an image, which preferably corresponds to the first image. The method also comprises determining a distance between an image detection element and the product based on the detected image and triangulation, and using the determined distance for determining the form and/or hole and/or groove configuration of the product.

By that the accuracy in the product control is further enhanced.

In yet another example the method further comprises projecting a laser line basically crosswise to the moving direction of the product. The method further comprises detecting the projected laser line on an image, which preferably corresponds to the first image. The method further comprises determining distance between an image detection element and several points along the projected laser line based on the detected image and triangulation and using the determined distances for determining whether the depth of the hole/-s and/or the groove/-s of the product is in agreement with a specification of the product.

By that additional control of the product is facilitated.

At least one of the objects is also achieved with a computer program for product control, where said computer program comprises program code for causing execution of any of the above mentioned methods.

At least one of the objects is also achieved with a computer program product comprising a program code stored on a computer-readable medium for performing any of the above mentioned methods.

Here, and in the whole description the expression retro-reflective means that the light is reflected back in the same direction where it came from, or at least almost the same direction where it came from.

BRIEF DESCRIPTION OF THE FIGURES

FIG. 4 shows a flowchart over the method according to the invention.

FIG. 5 shows a flowchart of a possible further development of the method according to the invention.

DETAILED DESCRIPTION OF VARIOUS EMBODIMENTS

Figure 1:
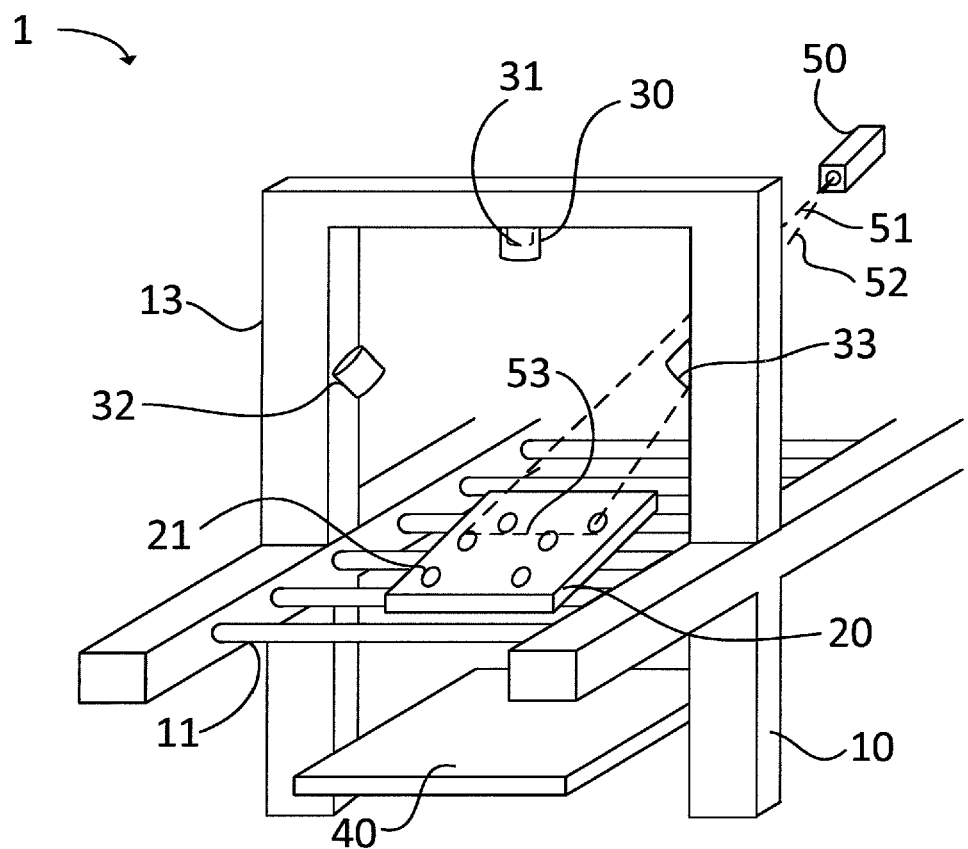
FIG. 1 shows schematically an embodiment of the arrangement according to the invention.

The arrangement according to the invention is most easily described with the help of a possible embodiment 1 which is schematically illustrated in FIG. 1. Embodiment 1 has especially been chosen to explain in a plain manner the object and the functioning of the invention. Not all parts of the embodiment 1 are needed to perform the invention. Instead, embodiment 1 does show several advantageous further developments of the invention.

In the possible embodiment 1 the product 20 is transported on a transport arrangement 10, 11. In the shown example the product is an essentially flat panel. The panel can be made of wood or metal. The product can also be made of plastic. The panel can also be made of other materials. The arrangement can preferably be used for flat products 20. In the shown example the product 20 comprises several holes 21, of which for the sake of clarity only one hole 21 has been marked by a reference number. The product can also comprise grooves. Grooves and/or holes can be situated on more than one side of the product. Potential holes 21 and/or grooves are in one example totally penetrating the whole product. In one example the potential holes 21 and/or grooves have a certain depth, but are not totally penetrating, i.e. one cannot "look through the product".

In the shown example the transport arrangement 10, 11 is made up of a support 10 and several rollers 11, of which for the sake of clarity only one roller 11 has been marked by a reference number. The rollers 11 can in one embodiment be turned electrically or mechanically so that a product 20 on the rollers is moved due to the kinetic energy which is transmitted to the product from the rollers. In one embodiment at least some of the rollers are connected with a band/belt. The band/belt is not shown in the figure. The band/belt can cause the connected rollers to rotate at the same speed. In such a way the transport arrangement comprises a conveyer belt. The band/belt will in that case preferably only be situated on a certain position at the rollers 11, for example at the side of the rollers at the support 10, so that the product 20, 21 is not or is basically not transported on the band/belt. The transport arrangement can in principle be any transport arrangement which does not totally embrace the product. It is important that the transport arrangement does not obscure the product in such a way that the light which is named in the following description is absorbed or reflected too much by the transport arrangement. In one example the transport arrangement 10, 11 is situated in a production line, for example after the product 20 has been supplied with holes 21 and/or grooves. Supplying the product with holes 21 can, for example, be achieved by means of a drill arrangement. In one example the transport arrangement 10, 11 is situated after the product has been supplied with a surface treatment, for example a surface coating. In one example the transport arrangement is used in a step before the product 20 is packed up. The product 20 can be a part of a bigger product and be packed up together with other products in a packaging arrangement.

In one example the product 20 is a part of a furniture which should be packed up together with other furniture parts after the product control.

The embodiment 1 comprises a first camera arrangement 31. The first camera arrangement 31 comprises in some embodiments several cameras. In other embodiments the first camera arrangement 31 comprises one camera. Preferably, the camera/-s in the first camera arrangement 31 and in potential further camera arrangements is/are digital cameras, for example cameras based on CMOS or on CCD-technique. In the embodiment 1 the first camera arrangement 31 is situated at a superstructure support 13. In other embodiments the first camera arrangement is situated at the ceiling. In yet other embodiments the first camera arrangement is situated on the floor. In yet other embodiments the first camera arrangement is situated at another element, for example at a wall or a camera arrangement support. Said placing possibilities for the first camera arrangement exist also for a potential second camera arrangement or for potential further camera arrangements. The first camera arrangement 31 is arranged to take at least one image of at least a part of the product when the product is in or at the transport arrangement 10, 11. In other words, the first camera arrangement 31 is arranged in such a way that at least a part of the product 20, 21 is in the field of view of the first camera arrangement 31 during the transport process. The embodiment 1 comprises also a first illumination arrangement 30. The first illumination arrangement 30 is arranged to emit light for detection of the first camera arrangement 31. In the shown embodiment 1 the first illumination arrangement 30 is arranged on the same side of the product 20 as the first camera arrangement 31. In one example the first illumination arrangement 30 comprise light emitting diodes, which preferably emit pulsed light. By using light emitting diodes a saving of energy can be achieved compared to light bulbs, halogen lamps, or similar light sources. By emitting pulsed light the life time of the light emitting diodes is increased. Further, the heat production in the light emitting diodes is reduced. The pulse frequency of the light emitting diodes is connected to the frequency for taking the images of the first illumination arrangement 30 in such a way that the light emitting diodes emit light during the time when the first camera arrangement 31 takes an image. Another advantage of the light emitting diodes is that the emitted light spectrum is limited compared to other light sources such as light bulbs or halogen lamps. By that the first illumination arrangement 31 can emit light in a certain wavelength range which can differ from the wavelength range of other light emitting diodes in a potential third illumination arrangement. The advantages of that will be explained later. In one example the first illumination arrangement is emitting stroboscopic light.

The embodiment 1 comprises a retro-reflective foil 40 which is arranged on an opposite side of the product 20, 21 in relation to the side of the first camera arrangement 31 and the first illumination arrangement 30. The retro-reflective foil 40 is arranged to reflect at least a part of the light which has been emitted by the first illumination arrangement 30 to the first camera arrangement 31. Here, and in the whole document, the expression retro-reflective foil should not only comprise a foil, but any retro-reflective element.

The first illumination arrangement 30 in embodiment 1 is arranged in such a way that the angle of incidence from the illumination is the same or nearly the same as the angle of observation for the first camera arrangement 31 for every point in its image plane. This implies that a beam of light which is emitted from the first illumination arrangement 30 and which is reflected by the retro-reflective foil 40 reaches to the first camera arrangement 31. This is achieved in embodiment 1 by the fact that the first illumination arrangement 30 is arranged in a circle around the first camera arrangement 31. By that, the first illumination arrangement 30 and the first camera arrangement 31 are at nearly the same position. In a preferred embodiment the light which is reflected from the retro-reflective foil 40 to the first illumination arrangement 30 gives rise to that the taken at least one image is overexposed on these places, whereas the light which reaches the first camera arrangement 31 through reflection from the product 20, 21 preferably gives rise to that the taken at least one image is underexposed on these places.

Figure 3A:
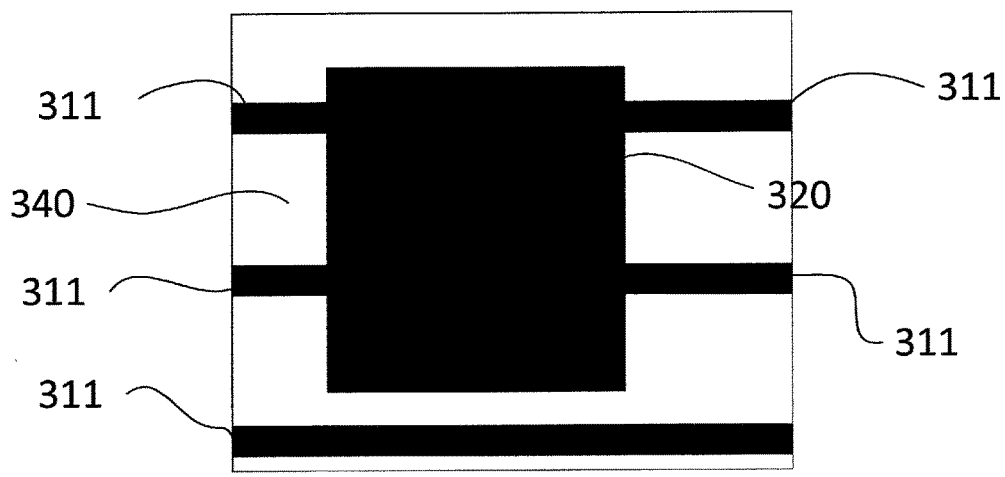
FIG. 3a shows a possible image of a product which has been taken by the first camera arrangement when the light from the first illumination arrangement has been sent.

The embodiment 1 comprises also a computation unit, which is not shown in FIG. 1. In one example, the computation unit is in or at the camera arrangement. In another example, the computation unit is at another place. In one example, the computation unit is an external computer. In one example the computation unit is integrated in a potential control arrangement for the production process. In one example the computation unit is arranged to communicate with a potential control arrangement for the production process and to transmit data to it. The computation unit is arranged to receive said at least one image from the first camera arrangement 31. The computation unit is further arranged to determine at least one geometrical property of the product 20 based on said at least one image. In one example said at least one geometrical property comprises at least a part of the outer contours of the product. This is in one example done through image processing, for example via software, in the computation unit. If the image is overexposed on the places which do not show the product 20 and underexposed on the places which show the product, such as described above, it is especially easy to differ between sections of the image which belong to the product 20 and sections of the image which do not belong to the product 20, and in such a way determining a geometrical property of the product 20, for example at least one of the outer contours of the product 20. An explicit example is shown in FIG. 3a.

In one example, the computation unit is also arranged to determine the location of the edges of the product in said at least one image. By that, the computation unit can determine the position and/or orientation of the product on or in the transport arrangement.

For achieving a high rate of production in a production arrangement it is often advantageous having high transportation speeds in the transport arrangement 10, 11 for being able to transport as many products 20 as possible through the production process during a certain period of time. The higher the transport speed the more easily it happens that a product 20 is turned on the transport arrangement 10, 11. If the product, for example, is rectangular and if the edges of the product at a certain moment of time during the transportation process were parallel to the transport arrangement, resp. perpendicular to the transport arrangement, said turning can cause the edges of the product at another moment of time no longer being parallel to the transport arrangement, respectively perpendicular to the transport arrangement. If the computation unit which has been described above determines the orientation of the product, that turning of the product can be detected.

In one example the computation unit is arranged to compare the determined at least geometrical property of the product with a pre-determined specification of the product. In one example the computation arrangement is arranged to communicate to a potential control arrangement of the production process whether a certain deviation between said at least one geometrical property and the pre-defined specification has been detected. In one example the computation unit is arranged to output a message in case a certain deviation between said at least one geometrical property and the pre-defined specification has been detected. The message can in one example be a message to an operator. In one example care is taken of the determined position and/or orientation of the product when said at least one geometrical property is compared with a pre-determined specification of the product. In one example, when the pre-determined specification is a template, the position and/or orientation of the product is adapted via image manipulation so that it is in accordance with the template. In such a way a comparison is facilitated and deviations between the product and the template can be detected. In another example a relative coordinate system is introduced for the product, where the origin, for example, is situated at a specific designated point of the product, for example a corner. Then, the geometrical properties of the product can be described in the relative coordinate system and can be compared with the geometrical properties of a corresponding relative coordinate system for the specification of the product. These examples are not exhaustive. Instead any comparison method resulting in the same or nearly the same result can be used here.

In one example at least one calibration object is arranged in the field of view of the first camera arrangement 31. This is not shown in the figure. Said at least one calibration object can, for example, be arranged at the same height as the rollers 11. In one example said at least one calibration is arranged between the rollers 11. In case the arrangement comprises more than one calibration object, these calibration objects are preferably arranged in such a way that their relative position is fixed. Said at least one calibration object is preferably partly retro-reflective and is arranged in such a way that the light which comes from the first illumination arrangement 30 is reflected from said at least one calibration object to the first camera arrangement 31. In such a way the first camera arrangement 31 can be calibrated without manual interference in the production process.

In one example the computation arrangement is arranged to compute at least some of the width, length, rectangularness, or form of the product. In one example said at least one geometrical property of the product comprises the width, length, rectangularness, or form of the product. The length, width, rectangularness, or form are often crucial for the functioning of the product. Therefore, one or more of these properties can be especially advantageous for a comparison with a specification of the product.

The embodiment 1 further comprises at least one second illumination arrangement 32, 33. In the embodiment 1 said at least one second illumination arrangement 32, 33 consists of a first and a second illumination arrangement 32 and another second illumination arrangement 33. In the embodiment 1 said second illumination arrangements 32, 33 are attached at the support 10. What has been said above regarding other possibilities of positioning the first illumination arrangement than attaching at the support is valid as well for the second illumination arrangements 32, 33. The second illumination arrangements 32, 33 are arranged in relation to the transport arrangement 10, 11 in such a way that light from the first illumination arrangement 32, 33 is reflected from the product 20 to the first camera arrangement 31.

In one example the second illumination arrangements 32, 33 are emitting stroboscopic light. Especially if the transportation speed of the product 20 is high, stroboscopic light with a relatively short time of light exposure and a relatively large amount of light ensures that the first camera arrangement 31 can take sharp images of the product. It is known for a person skilled in the art how the amount of light and the time of light exposure can be adapted in relation to a specific camera arrangement in such a way that sharp images of an object, in this case the product 20, can be achieved. Therefore, this adaption is not described here any further.

In embodiment 1 the computation unit is further arranged to determine the hole and groove configuration 21 of the product 20 on the side which is faced to the first camera arrangement 31. This determination is based on said at least one image. The hole and groove configuration comprises preferably the presence of potential holes 21 and potential grooves, and/or the position of potential holes 21 and potential grooves in relation to the product, and/or the size of potential holes 21 and potential grooves. Said at least one image which is taken by the first camera arrangement 31 is preferably not over- or underexposed when the light from the second illumination arrangement 32, 33 is detected. Holes 21 and/or grooves will in such a way receive a different colour or a different grey scale than the rest of the product 20. This is seen, for example in FIG. 3c. FIG. 3c also shows the outer contours of the panel which are achieved in the way that said first and said at least one second illumination arrangement illuminate at the same time. Through, for example, automatic image processing which is detecting sufficient high contrast changes and/or colour/grey scale changes, the presence, size and position of potential holes 21 or grooves can in such a way be detected. The presence, size, and position of potential holes 21 or grooves of the product are then in one example compared with a specification of the product 20. This is in one example done in a kind corresponding to what has been described above in relation with the at least one geometrical property of the product. Even potential messages to an operator and/or communication to a potential control arrangement for the production process can be sent based on the result of the comparison in the same kind as described above.

The embodiment 1 further comprises a first laser arrangement 50. The first laser arrangement 50 is arranged in such a way that it projects at least a first laser line 53 on the product 20. The first laser arrangement 50 is fastened at a suitable place in or after the production line. In one example, the suitable place is a support, a wall, the floor or the ceiling. The first laser arrangement 50 is arranged in such a way that its distance to the first camera arrangement 31 and to the pointing direction of the first laser arrangement 50 is known. In one example, these values are measured or determined at the installation of the arrangement or through a calibration process. In another example these values are determined continuously or in certain intervals during the production control. Said at least one first laser line 53 is projected basically crosswise to the direction of transportation of the transport arrangement 10, 11 in such a way that said at least one first laser line 53 at least partly is in the field of view of the first camera arrangement 31. Said at least one first laser line 53 has a wavelength which can be detected by the first camera arrangement 31.

The first laser arrangement 50 is arranged in such a way that an imagined triangle is formed between the first laser arrangement 50, the first camera arrangement 31 and the product 20. In other words, the first laser arrangement 50, especially a specific point at the first laser arrangement 50, for example the point where the laser light leaves the first laser arrangement, the first camera arrangement 31, especially a point at the first camera arrangement, for example a specific point in the image sensor of the first camera arrangement 31, and the product 20, especially an arbitrary point of the part of said at least one first laser line 53 which ends on the product 20, constitute the corners of the imagined triangle. Preferably none of the distances in the imagined triangle is substantially longer or shorter than a different distance in the same imagined triangle. Further, the computation unit is arranged to compute a distance between the product 20, especially a point of the part of said at least one first laser line 53 which ends on the product 20, and the first camera arrangement 31 based on triangulation. This computation is performed via triangulation with help of the known distance between the first camera arrangement 31 and the first laser arrangement 50, the pointing direction of the first laser arrangement 50 and the placing of said first laser line 53 on said received at least one imagine. This distance can be determined with high accuracy. The accuracy is increased the higher the resolution is of the first camera arrangement 31. A person skilled in the art realises also that a good compromise between accuracy and the space for the described embodiment 1 would be that the length of the three sides of the triangle is approximately equal. In case the distance between the first camera arrangement 31 and the first laser arrangement 50 is much shorter than the two other sides in the imagined triangle the accuracy will be deteriorated. If the distance between the first camera arrangement 31 and the first laser arrangement 50 is much larger than the two other sides in the imagined triangle, the space which is needed for the arrangement is increased. A person skilled in the art will understand to optimise the arranging of the first camera arrangement 31 and the first laser arrangement 50 according to the circumstances.

Since high transport speeds can occur in the transport arrangement 10, 11, the product 20 can slightly jump up and down due to the effect of the rollers in such a way that, assuming a flat transport path and a flat product, a front edge of the product is somewhat elevated and a rear edge of the product is somewhat lowered during a moment of time in the transportation process, or vice versa. This bouncing, however, causes that the geometry of the product change in said at least one image. A bouncing, for example, results in one example in that the length of the product, as it is detected in the image, is changed. In one example the bouncing changes the distance between the holes 21 of the product 20, as it is detected in the image, is changed. If the demand on the accuracy of the hole positions is high, for example a tenth or some tenths of a millimeter, or even smaller, such a bouncing can easily influence the result of a comparison of the kind described above, for example since the values determined from the computation unit are outside the specification of the product 20. By determining the distance between the product 20 and the first camera arrangement 31 as described above, a bouncing of the product 20 can be detected. The computation unit does then in one example consider that calculated distance and corrects the determined values based on said calculated distance.

In one example the computation unit is further arranged to identify damages on the surface of the product 20 based on said at least one image. Preferably light arising from the two second illumination arrangements 32, 33 and detected by the first camera arrangement 31 after reflection on the product 20 is used for that. In such a way, the part of the image which facilitates for the computation unit to detect damages on the surface will be neither over- nor underexposed.

Figure 2:
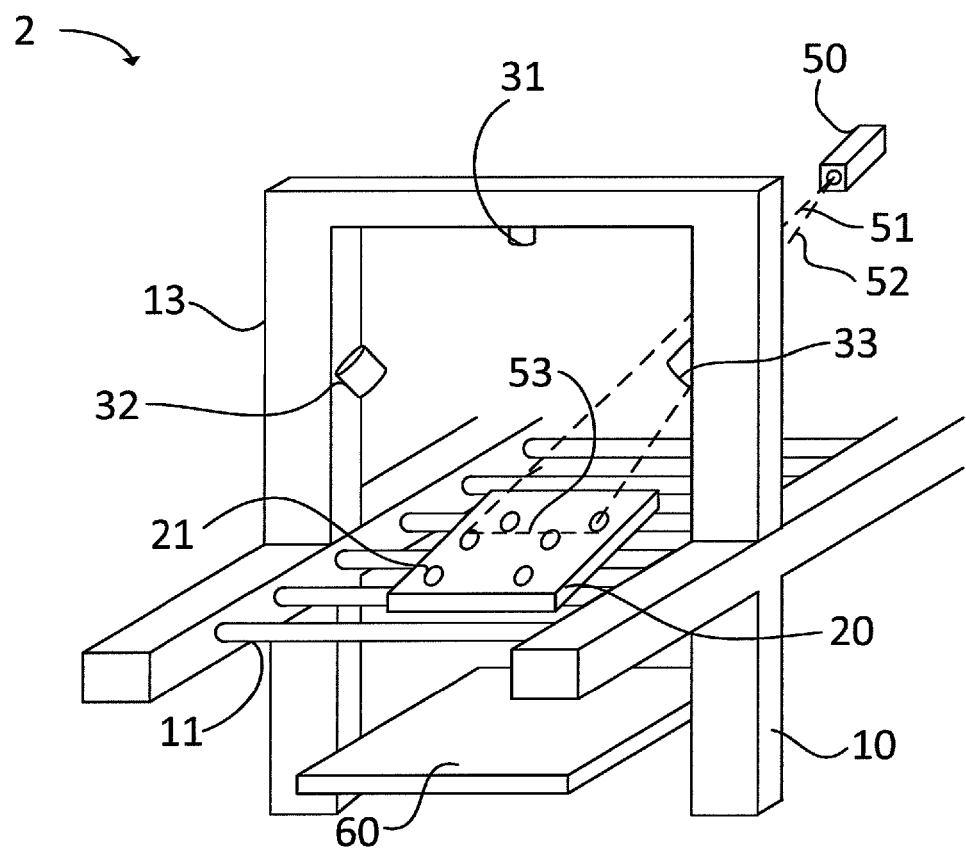
FIG. 2 shows schematically another embodiment of the arrangement according to the invention.

FIG. 2 shows another embodiment 2 of the arrangement according to the invention. In this embodiment, elements with the same reference number are the same as in FIG. 1 and are thus not described here once again, as long as their functioning does not differ from the embodiment 1. In embodiment 2, a first illumination arrangement is denoted 60 which is arranged to emit light for detection by the first camera arrangement 31. In embodiment 2, the first illumination arrangement 60 is arranged on the side which is opposite the first camera arrangement 31. The first illumination arrangement 60 comprises preferably a luminous screen 60. The first camera arrangement 31 detects then light which has arrived there from the luminous screen 60 without having been blocked by the product 20. In such a way an image similar to FIG. 3a is achieved as well, and the computation unit works in a similar way as has been described in relation to embodiment 1.

In the following additional further developments of the arrangement according to the invention are described. These further developments are not shown in FIG. 1 or FIG. 2, but are described in relation to these figures for increasing understanding of the invention.

In a possible further development the arrangement comprises a second laser arrangement. This second laser arrangement is arranged to project a second laser line on the product basically crosswise to the transporting direction of the transport arrangement in such a way that the second laser line at least partially is in the field of view of the first camera arrangement. The second laser arrangement is further arranged to form an imagined triangle between the second laser arrangement, the first camera arrangement, and the product. The imagined triangle with the second laser arrangement is formed in total analogy to the imagined triangle of the first laser arrangement. The difference is that the distance between the second laser arrangement and the first camera arrangement in the imagined triangle preferably is substantially shorter than the two other distances in the imagined triangle. The computation unit is then further arranged to compute a distance between the product and the first camera arrangement at many points along the second laser line based on triangulation. The triangulation is performed with the help of the known distance between the first camera arrangement and the second laser arrangement, the pointing direction of the second laser arrangement and the placing of the second laser line on said received at least one image. Since the distance is calculated at many points along the second laser line one gets an elevation profile of the product along the second laser line. If this is done with many other laser lines, alternatively if this is done many times at different places of the product, one can combine the elevation profiles for achieving elevation profiles of the whole or parts of the product. In one example the arrangement is configured to send the second laser line to many other places of the product and the computation unit is arranged to calculated the distance between the product and the first camera arrangement at many points along the laser line every time the laser line is at a new place of the product. The computation unit is then in one example arranged to determine an elevation profile of the whole or parts of the product based on the calculated distances at many points along the laser line each time the laser line is at a new place of the product. The computation unit is in the described embodiment then further arranged to determine the depth of potential holes or grooves based on the computed distance between the product and the first camera arrangement at many points. In one example the computation unit is then arranged to compare the determined hole and/or groove depth with a specification of the product.

Since the distance between the second laser arrangement and the first camera arrangement in the imagined triangle preferably is substantially shorter than the two other distances in the imagined triangle, the other laser arrangement is preferably much closer to the first camera arrangement than a potential first laser arrangement. This results in the second laser line reaching the bottom of potential holes and/or grooves more easily. Especially this is achieved in case the product is flat or basically flat and potential holes and/or grooved are arranged perpendicular or basically perpendicular to the flat or basically flat surface of the product. Admittedly the height resolution will be deteriorated, as has been described in relation to the first laser arrangement, but the depth of potential holes and/or grooves usually don't need to be determined as accurate as the position and/or size of potential holes and/or grooves.

In one example, taking the image with the first camera arrangement happens when both said first and said at least one second illumination arrangement emit light. FIG. 3c shows an image which has been taken in such a way. By that it is achieved that at least one geometrical property of the product and a potential hole and/or groove configuration are determined in the same image. By doing the determination in the same image it is assured that both said at least one geometrical property of the product and said potential hole and/or groove configuration automatically are in the same coordinate system. In such a way no errors will occur due to a relative position change.

In one example simultaneous takings of the first camera arrangement and the second camera arrangement are performed, whereby the position for the hole and groove configuration from the underside can be calculated in relation to the outer contour of the panel.

In one example the image taking from the first camera arrangement is not performed simultaneously when all potential illumination arrangement and/or laser arrangements emit light. In one example the image taking of the first camera arrangement with light originating from the first illumination arrangement happens at another moment of time than the image taking of the first camera arrangement with light originating from the second illumination arrangement. In such a way, the computation unit can use one image for determining at least one geometrical property of the product, whereas the computation can use the other image for determining the hole and/or groove configuration.

In certain situations potential deviations between the product and a specification do not need to be discovered at every product, but it suffices to discover systematic deviations of the production. Especially in this case the possibility of not determining all possible deviations at every image taking can be advantageous for optimising the settings of the arrangement to detect the deviation on which one is most interested at present. Such an optimisation is for example the settings of the first camera arrangement, for example its time of illumination and/or its frequency for taking the images.

In one example the taking of images happens when the second laser arrangement projects said second laser line on the product simultaneously to when one or several second illumination arrangements and/or laser arrangements emit light. In this example, the frequency of taking images can, for example, be increased drastically for getting the second laser line on many places of the product. In one example, the first camera arrangement takes in the order of magnitude 1000 pictures per second while the product is transported along the first camera arrangement, for thus getting an elevation profile of the whole or parts of the product.

In another further development the arrangement according to the invention comprises a second camera arrangement and third illumination arrangement. The second camera arrangement is arranged to take at least one image of at least a part of the product while the product is in or at the transport arrangement. The third illumination arrangement is arranged in relation to the transport arrangement in such a way that light from said third illumination arrangement is reflected from the product to the second camera arrangement. The second camera arrangement is arranged on the side of the product which is opposite the first camera arrangement.

This implies that the other camera arrangement is arranged under the product 20 in a further development of embodiment 1 or 2. The third illumination arrangement is then in one example arranged under the product 20. In one example, when the third illumination arrangement is arranged under the product, the third illumination arrangement and the second camera arrangement are arranged in analogy to what has been described above in relation to the first illumination arrangement and the first camera arrangement.

The computation unit is in the described further development further arranged to receive at least one image from the second camera arrangement and to determine the hole and groove configuration on the side which is faced to the second camera arrangement based on said at least one image from the second camera arrangement. This happens in full analogy to what has been described above regarding determining the hole and/or groove configuration of the product on the side which is faced to the first camera arrangement. By letting the second camera arrangement take and image simultaneously to when the first camera arrangement takes an image, the hole and/or groove configuration on the side faced to the second camera arrangement is calculated in relation to the outer contours of the panel.

The first and the second camera arrangement are advantageously arranged in such a way that both camera arrangements only occupy a small part or no part at all of the field of view of the respective other camera arrangement. This is achieved in one example through that the camera arrangements have small size. This is achieved in one example through the distance between the camera arrangements being large. This is achieved in one example through one camera arrangement often being covered by the product in the field of view of the other camera arrangement. Even for the illumination arrangements it applies that they preferably are not visible in the field of view of a camera arrangement. This can in one example be achieved in the same way as just have been described for the camera arrangements.

In one example the taking of the images of the second camera arrangement is synchronised in time with the taking of the image of the first camera arrangement. By that the computation unit can use the determined at least one geometrical property of the product which has been achieved through said at least one image of the first camera arrangement for achieving a better or additional information from said at least one image from the second camera arrangement.

In yet another further development of the invention, when it comprises the first and the second camera arrangement, the first illumination arrangement and said potential at least one second illumination arrangement are arranged to emit light with a first wavelength or with a first wavelength range. In one example this is done by using a filter arrangement in connection with the first illumination arrangement and/or said potential at least one second illumination arrangement. The filter arrangement is then letting only said first wavelength or said first wavelength range pass through. In one example said first and/or said potential at least one illumination arrangement comprise light emitting diodes. In one example the light emitting diodes only emit in a first wavelength arrangement. In said further development, the third illumination arrangement is arranged to emit light with a second wavelength or in a second wavelength range, where the second wavelength or the second wavelength range is different from the first wavelength or the first wavelength range, respectively. The first camera arrangement is further arranged to detect light basically outside the first wavelength or the first wavelength range and the second camera arrangement is further arranged to detect light basically outside the first wavelength or the first wavelength range. In such a way it is prevented that the first camera arrangement considerably detects light from said first and said potential at least one second illumination arrangement. By that one does not have to consider said first and said potential at least one second illumination arrangement in said at least one image from the second camera arrangement.

In one example of the arrangement according to the invention which comprises rollers 11 or other element of a transport arrangement which can be seen when a camera arrangement takes images of the product, the first and/or the potential second camera arrangement is arranged to take several images of the product. This is done in such a way that different parts of the product are on a roller 11 or on or in another element of the transport arrangement at different images. By that one can achieve that most or even all parts of the product are not covered by the transport arrangement on at least one image. The computation arrangement is then in one example arranged to combine these images.

FIG. 3a shows a possible image of a product which has been taken by the first camera arrangement when the light from the first illumination has been sent.

Figure 3B:
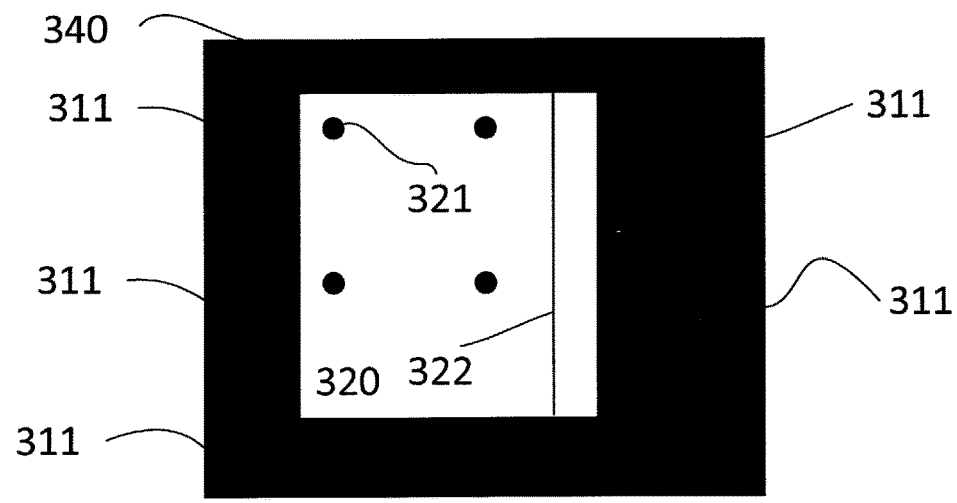
FIG. 3b shows a possible image of a product which has been taken by the first camera arrangement when the light from said at least one second illumination arrangement has been sent.
Figure 3C:
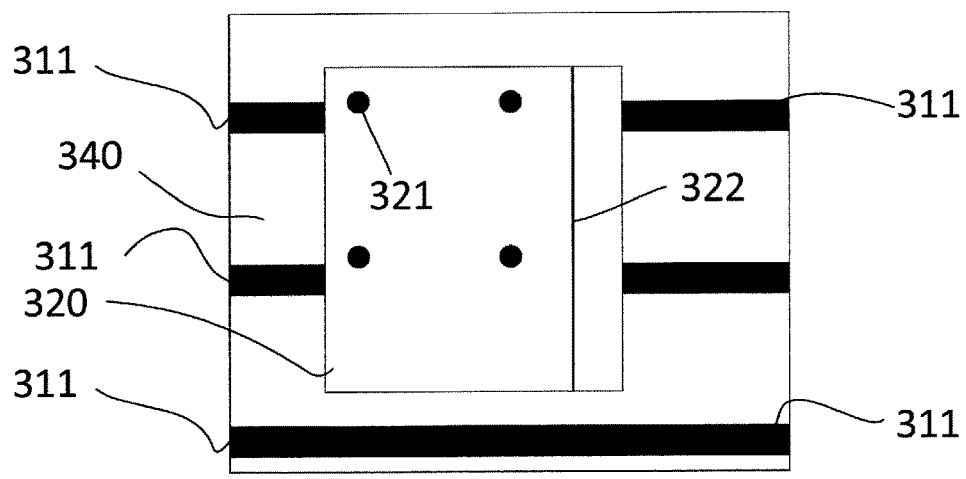
FIG. 3c shows a possible image of a product which has been taken by the first camera arrangement when the light from both the first illumination arrangement and from said at least one second illumination arrangement has been sent.

FIG. 3b shows a possible image of a product which has been taken by the first camera arrangement when the light from said at least one second illumination arrangement has been sent.

FIG. 3c shows a possible image of a product which has been taken by the first camera arrangement when the light from both the first illumination arrangement and from said at least one second illumination arrangement has been sent.

In the FIG. 3a-3c reference number 311 denotes the rollers of a transport arrangement, for example of a transport arrangement 10, 11 as has been schematically sketched in FIG. 1 or FIG. 2. In FIG. 3a-3c the product 320 and a luminous screen 340 or a retro-reflective foil 340 is also shown. In FIG. 3b-3c also holes 321, of which only one hole 321 has been marked for the sake of clarity, are shown. Even a groove 322 is shown in FIG. 3b-3c.

If the image according to FIG. 3a has been taken with the arrangement according to FIG. 1, the white colour of the retro-reflective foil 340 originates from the fact that the light which has been emitted by the first illumination arrangement, has been retro-reflected by the retro-reflective foil mainly to the first camera arrangement and in such a way has overexposed the image, while the light from the first illumination arrangement which has been emitted to the product 320 has been reflected to many different directions, especially away from the first camera arrangement, whereby the part of the light which has been retro-reflected to the first camera arrangement is very small and thus has underexposed the image. For the rollers 311 the same applies as for the product 320.

In case the image according to FIG. 3a has been taken with an arrangement according to the invention according to FIG. 1, the white colour of the luminous screen originates from the fact that the light therefrom directly reaches the first camera arrangement and by that has overexposed the image there. The black colour from the product 320 originates from the fact that the light which has been emitted by the luminous screen 340 has been blocked by the product 340 from reaching the first camera arrangement, resulting in that the image has been underexposed there. For the rollers 311 the same applies as for the product 320.

In FIG. 3b no light has been emitted from the first illumination arrangement, whereby the illuminous screen 340 is turned off and therefore dark on the image, resp. no light has been retro-reflected from the retro-reflected foil 340 to the first camera arrangement. The light which has been emitted by the second illumination arrangement has been reflected by the product in many directions, among others to the first camera arrangement, resulting in the product 320 being visible on the image. For the rollers 311 the same applies as for the product 320.

Since the situation under which the image in FIG. 3c has been taken corresponds to a combination of the situation in FIG. 3a and FIG. 3b, i.e. in FIG. 3a the first illumination arrangement has emitted light, in FIG. 3b the second illumination has emitted light, and in FIG. 3c the first and the second illumination arrangement has emitted light, thus also the image of FIG. 3c is a combination of the images from FIG. 3a and FIG. 3b.

FIG. 4 shows a flowchart over the method 400 according to the invention. The method starts with step 410. In step 410 first light is emitted to the product from at least a first side in such a way that a part of the first light reaches the product and the other part of the first light basically is retro-reflected from a surface which is situated on the opposite side of the product. This surface is, for example, a retro-reflective foil as has been described above in connection to embodiment 1. The expression to the product does thus not mean that all emitted light should reach the product, but only that a part of the emitted light should reach the product. This can, for example, be achieved if the product is, at least partly, in a light cone of an illumination arrangement, whereas the product does not cover the whole light cone. The method continues with step 420.

In step 420 a first image of the product is detected on basically the same side of the product from which the first light is emitted. The detection is in such a way that the angle of incidence from the illumination is the same or basically the same as the angle of observation for each point in the image plane. In one example this is achieved when the first image is detected at the same place or nearly the same place as the top of the light cone. The light cone is in one example the same light cone which has been described in relation to step 420. The method continues with step 430.

In step 430 edge information is extracted from the first detected image. This is, in one example, done via image processing routines. In an advantageous way, this information is extracted automatically. In one example, edge information comprises at least some of the presence, position and orientation of at one or several edges. In one example, said one or several edges are at least one of the one or several outer edges of the product. The method continues with step 440.

In step 440 the form and/or position and/or orientation of the product is determined in the image based on the extracted edge information.

In one example the method finishes after step 440. In another example the method continues with step 450 after step 440.

In step 450 it is determined whether the geometry of the product is in agreement with a pre-defined specification of the product based on the determined form and/or position and/or orientation. In one example this is done in the same way as has been described above in relation to FIG. 1 and FIG. 2. In one example the geometry of the product comprises at least one of the width, length, rectangularness, and/or other two-dimensional form of the product. The method finishes after step 450.

In one example the method 400 comprises a further method 500 which is shown and described in relation to FIG. 5. The method 500 is performed in one example simultaneously with the method 400. In one example, the method 500 is performed before or after the method 400. The method 500 starts with step 510.

In step 510 the product is additionally illuminated from one or several angles which preferably don't differ with more than 90 degrees from the direction from which the first light is emitted. This additional illumination is in one example done simultaneously as the first light is emitted. In one example the additional illumination is not done as the same time as the first time is emitted. Since the direction of the light which additionally illuminates the product does not differ with more than 90 degrees from the direction from which the first light is emitted, it is assured, especially in case the product is flat or basically flat, that the light from the additional illumination, after reflection on the product, can be caught in the same image which has been taken in step 420, or at least in another image taken at the same place as in step 420. The method continues with step 520.

In step 520, in an image, which preferably is the first image, the light from the additional illumination is detected which has been reflected there from the product. If this detection happens simultaneously, an image as in FIG. 3c can be achieved. If the image is the first image, the method ensures that potential determinations in step 450 and/or in step 530 are done based on the same image, and thereby at the same moment of time during the transport process of the product. The method continues with step 530.

In step 530 it is determined whether the hole and/or groove configuration of the product is in agreement with a specification of the product based on the detected image. In one example the hole and/or groove specification of the product comprises at least some of the presence and/or position and/or size of the holes and/or grooves. This is in one example done as described above in relation to FIG. 1 and FIG. 2. In one example, when the image from step 520 for example is the same image as the first image from step 420, a determination of the hole and/or groove configuration of the product based on the determination of the geometry in step 450 is facilitated. In one example, it is hereby facilitated to relate the hole and/or groove configuration of the product to the geometry of the product. The method 500 ends after step 530.

Figures 6, 7:
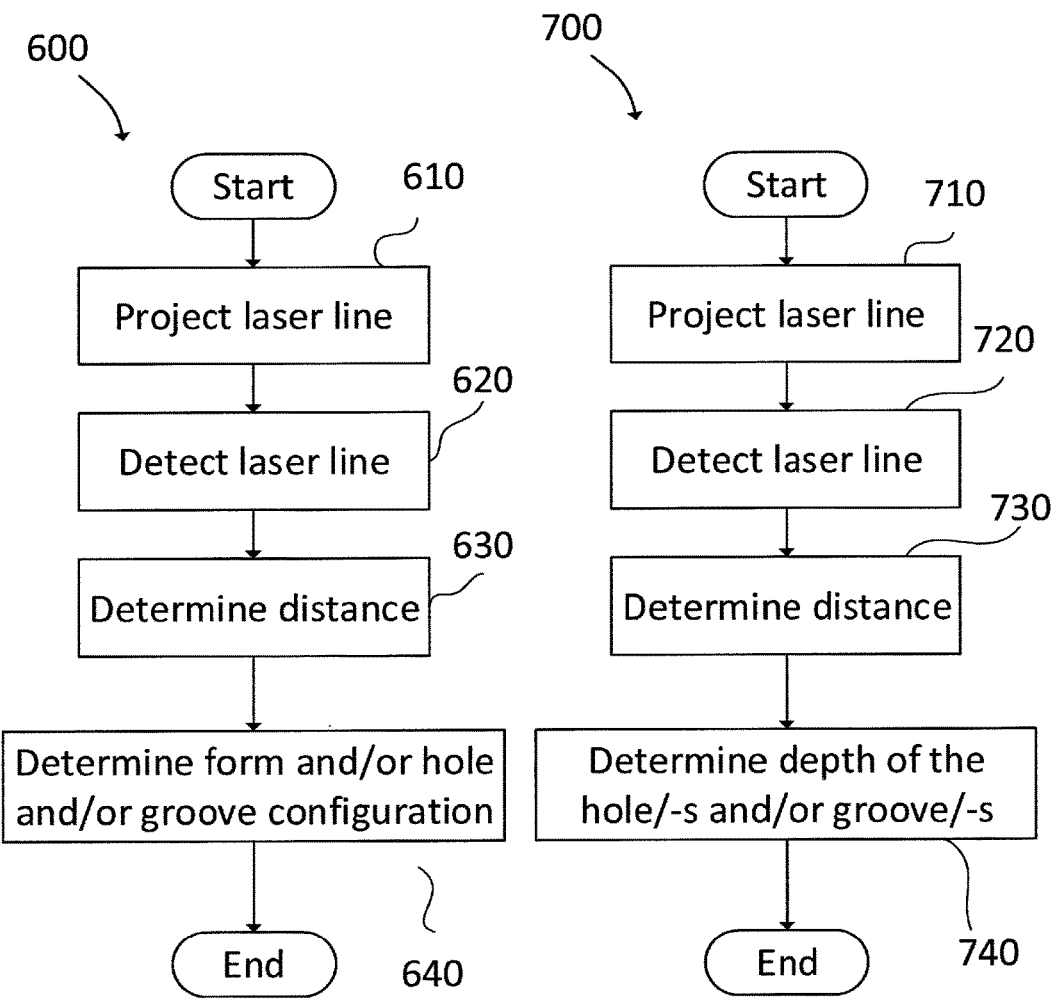
FIG. 6 shows a flowchart of yet a further possible development of the method according to the invention.
FIG. 7 shows a flowchart of yet a further possible development of the method according the invention.

In one example, the method according to the invention is further developed with a method 600 as illustrated in FIG. 6. The method 600 is in one example performed simultaneously as the method 400. In one example the method 600 is performed before or after the method 400. The method 600 starts with the step 610.

In step 610 at least one laser line is projected basically crosswise to the moving direction of the product.

In a subsequent step 620 said projected at least one laser line is detected in an image. The image preferably corresponds to the first image. In one example the image is the first image. In one example the image is taken at the same place as the first image, preferably by the same camera. By that it is assured that optical errors and/or imaging properties are basically the same in step 620 and in step 420 so that the need for image correction is minimised.

In a subsequent step 630 a distance between an image detection element and the product is determined based on the detected image and triangulation. In an advantageous example the laser line is projected in step 610 in such a way that distance change between an image detection element and the product easily can be seen in the image of said detected at least one laser line. An example of how that can be achieved has been described in relation to FIG. 1 and FIG. 2.

In a subsequent step 640 the determined distance is used for determining the form and/or hole and/or groove configuration of the product. This step is performed before a potential step 530 is performed in a potential method 500. This step is also performed before step 440 is performed in case the distance is used for determining the form of the product. By using the distance, the values for the form and/or the position and/or the orientation and/or the hole and/or groove configuration can, in one example, be corrected for potential bounces of the product, or generally for potential rotations of the product around axles which are perpendicular to the optical axis of the camera arrangement which takes said image and/or first image in one of the steps 420, 520 and/or 620. Even this has been described in relation to FIG. 1 and FIG. 2. The method 600 ends after step 640.

In yet a further development of the method according to the invention the method 700 is used. The method 700 is, in one example, performed simultaneously with the method 400. In one example the method 700 is performed before or after the method 400. The method 700 starts with step 710.

In step 710 a laser line is projected basically crosswise to the moving direction of the product. The laser line is preferably constituted by another laser line than the laser line in a potential step 610.

In the subsequent step 720 the projected laser line is detected on an image, which preferably corresponds to the first image. In one example the image is taken at the same place as the first image, preferably by the same camera. This leads to the same advantages which have been discussed in connection to step 620.

In a subsequent step 730 a distance between an image detection element and several points along the projected laser line is determined based on the detected image and triangulation. By that an elevation profile of the product along the laser line is achieved. In one example one or several laser lines at many places of the product are used for getting an elevation profile of the whole or parts of the product. An example of how that can be achieved has been described in relation to FIG. 1 and FIG. 2.

In a subsequent step 740 the determined distances are used for determining whether the depth of the hole/-s and/or the groove/-s of the product is in agreement with a specification of the product. An example for how this can be achieved has been described in relation in relation to FIG. 1 and FIG. 2. The method ends after step 740.

In yet a further development of the method according to the invention a pattern having a plurality of points is projected on the product. The projection is preferably done via a laser projection. In a subsequent step at least a port of said projected pattern is detected on an image, which preferably corresponds to the first image. In a subsequent step a plurality of distances between an image detecting element and respective point out of the pattern which is projected on the product is determined based on the detected image and triangulation. The image detection element is, for example, said first camera arrangement 31. This triangulation is preferably done via a known distance between the arrangement which projects the pattern, for example a laser arrangement, and an image detection element, via a known direction between the arrangement which projects the pattern and respective point, as well as via a known direction between respective point and the image detection element. In such a way a plurality of distances is achieved, where every distance is a distance between a point on the product and the image detection element. In a subsequent step it is determined whether the product is bent or turned based on said plurality of determined distances. Since said plurality of distances and direction between the image detection element and the respective point in the pattern which has been projected on the product is known, one can calculated whether all projected points are in a plane or not. If these points are not in a plane, one can calculate their deviation from an imagined plane. In such a way one can decide whether an imagined flat product has been bent and/or turned. Such a bending and/or turning can, for example, occur for wooden products made of solid wood if the moisture from these wooden products is evaporating at different speeds on different places. In one example the height position of the product is determined based on said plurality of determined distances. With height position, it is intended here the distance between the product and the transport arrangement. In case the transport arrangement consists of transport rollers, the product is ideally directly situated on the transport rollers. It can, however, happen that the product bounces on the transport arrangement and one end of the product therefore is not directly situated on the transport arrangement, but instead is lifted from the transport arrangement. In such a way the product will be moved closer to the camera arrangement. By determining the height position, a potential computation unit can take a potential bouncing or another change in the height into account and correct for these effects when a geometrical property of the product is determined.

Above named embodiments and examples are possible to combine. A person skilled in the art will realise that the arrangement according to the invention or the method according to the invention can be adapted to best correspond to the control of a specific product.

The invention claimed is:

1. Arrangement for product control of a product (20, 21), during or after a production process, at a transport arrangement (10, 11) configured to transport the product (20, 21) to be controlled, wherein the arrangement comprises: a first camera arrangement (31) positioned on one side of the product (20, 21) and configured to take at least one image of at least a part of the product (20, 21) when the product is in or at the transport arrangement (10, 11), a first illumination arrangement (30; 60) configured to emit light for detection by the first camera arrangement (31), at least one second illumination arrangement (32, 33) arranged in relation to the transport arrangement (10, 11) in such a way that light from said at least one second illumination arrangement (32, 33) is reflected from the product (20, 21) to the first camera arrangement (31), and a computation unit configured to receive said at least one image from the first camera arrangement (31) and to determine at least one geometrical property of the product (20, 21) based on said at least one image, wherein the computation unit further is configured to determine a groove and hole configuration (21) of the product (20, 21) on the side which is faced to the first camera arrangement (31) based on said at least one image, the groove and hole configuration (21) comprising the presence of at least one of: potential holes (21) and potential grooves, the position of potential holes (21) and potential grooves in relation to the product, or the size of potential holes (21) and potential grooves (21).

2. The arrangement according to claim 1, wherein: the first illumination arrangement (30) is positioned on the same one side of the product as the first camera arrangement (31) and where the first illumination arrangement (30) is arranged in relation to the first camera arrangement (31) in such a way that the angle of incidence from the illumination is the same or nearly the same as the angle of observation for the first camera arrangement (31) for each point in the image plane of the camera arrangement (31), and the arrangement further comprises a reflective element (40) positioned on a side of the product (20, 21) that is opposite the one side of the product (20, 21) where the first camera arrangement (31) is positioned, such that the product (20, 21) is positioned intermediate the reflective element and at least one of the first camera arrangement and the first illumination arrangement, said reflective element (40) being arranged to reflect at least a part of the light which is sent from the first illumination arrangement (30) to the first camera arrangement (31).

3. The arrangement according to claim 1, wherein at least one calibration object is arranged in the field of view of the first camera arrangement (31), wherein said at least one calibration object is partly retro-reflective and is arranged in such a way that the light arriving from the first illumination arrangement (30) is reflected from said at least one calibration object to the first camera arrangement (31).

4. The arrangement according to claim 1, wherein the computation unit further is arranged to determine the location of the edges of the product (20, 21) in said at least one image and thereby the position and/or orientation of the product (20, 21) on or in the transport arrangement (10, 11).

5. The arrangement according to claim 1, where said at least one geometric property comprises at least a part of the outer contours of the product (20).

6. The arrangement according to claim 1, wherein the computation unit is configured to calculate at least some of the width, length, rectangularness, or form of the product (20).

7. The arrangement according to claim 1, wherein the first illumination arrangement (30) comprises light emitting diodes that emit pulsed light.

8. The arrangement according to claim 1, wherein the taking of the image by the first camera arrangement (31) is done when both said first illumination arrangement (30) and said at least one second illumination arrangement (32, 33) illuminate the product (20, 21) simultaneously.

9. The arrangement according to claim 1, wherein said at least one second illumination arrangement (32, 33) emits stroboscopic light.

10. The arrangement according to claim 1, further comprising:
a second camera arrangement configured to take at least one image of at least a part of the product (20, 21) while the product is situated in or on the transport arrangement (10, 11); and
a third illumination arrangement, arranged in relation to the transport arrangement (10, 11) in such a way that the light of said third illumination arrangement is reflected from the product (20, 21) to the second camera arrangement,
wherein:

the second camera arrangement is situated on the side of the product (20, 21) which is opposite to the first camera arrangement (31), and the computation unit further is configured to receive at least one image of the second camera arrangement and to determine the groove and hole configuration (21) of the product on the side which is faced to the second camera arrangement based on said at least one image from the second camera arrangement.

11. The arrangement according to claim 10, wherein the taking of the image of the second camera arrangement is synchronised in time with the taking of the image of the first camera arrangement (31) and wherein at least one second calibration object with a fixed relation to said first calibration object is arranged in the field of view of the second camera arrangement.

12. The arrangement according to claim 10, wherein the first illumination arrangement (30) and the second illumination arrangement (32, 33) are configured to emit light at a first wavelength or at a first wavelength range, and where the third illumination arrangement is configured to emit light at a second wavelength or at a second wavelength range, where the second wavelength or the second wavelength range is different from the first wavelength or the first wavelength range, respectively, and wherein the first camera arrangement (31) is configured to detect light essentially outside the second wavelength or the second wavelength range, and wherein the second camera arrangement is configured to detect light essentially outside the first wavelength or the first wavelength range.

13. The arrangement according to claim 1, further comprising a first laser arrangement (50) configured to project at least a first laser line (53) on the product (20, 21) basically crosswise to the transport direction of the transport arrangement (10, 11) in such a way that said first laser line (53) at least partially is in the field of view of the first camera arrangement (31), wherein the first laser arrangement (50) further is arranged to form an imagined triangle between said first laser arrangement (50), said first camera arrangement (31) and the product (20, 21), wherein no distance in the imagined triangle is substantially longer or shorter than another distance in the imagined triangle, and wherein the computation unit further is configured to compute a distance between the product (20, 21) and the first camera arrangement (31) based on triangulation with the help of the known distance between the first camera arrangement (31) and the first laser arrangement (50), the pointing direction of the first laser arrangement (50), and the placing of the first laser line (53) on said received at least one image.

14. The arrangement according to claim 1, further comprising a first laser arrangement (50) configured to project at least a pattern having a plurality of points on the product (20, 21) in such a way that said pattern at least partially will be in the field of view of the first camera arrangement (31), wherein the first laser arrangement (50) further is arranged in relation to the product (20, 21) and the first camera arrangement (31) in such a way that a plurality of imagined triangles are formed, wherein each imagined triangle out of said plurality of imagined triangles relates to an imagined triangle between said first laser arrangement (50), said first camera arrangement (31) and one of said plurality of points in the pattern which is projected on the product (20, 21), wherein no distance in each imagined triangle out of the plurality of imagined triangles is substantially longer or shorter than a different distance in the same imagined triangle, and wherein the computation unit further is configured to compute in the imagined triangles the distance between respective point in the pattern which is projected on the product (20, 21) and the first camera arrangement (31) based on the known distance between the first camera arrangement (31) and the first laser arrangement (50), the pointing direction of the first laser arrangement (50) for the respective point in the pattern which is projected on the product (20, 21) and the respective placing of the respective point in the pattern which is projected on the product (20, 21) on said received at least one imagine.

15. The arrangement according to claim 1, further comprising a second laser arrangement which is configured to project a second laser line on the product (20, 21) basically crosswise to the transporting direction of the transport arrangement (10, 11) in such a way that the second laser line at least partially is in the field of view of the first camera arrangement (31), wherein the second laser arrangement further is arranged to form an imagined triangle between the second laser arrangement, the first camera arrangement (31), and the product (20, 21), wherein the distance between the second laser arrangement and the first camera arrangement (31) in the imagined triangle is substantially shorter than the two other distances in the imagined triangle, and wherein the computation unit further is configured to compute a distance between the product (20, 21) and the first camera arrangement (31) at many points along the second laser line based on triangulation with the help of the known distance between the first camera arrangement (31) and the second laser arrangement, the pointing direction of the second laser arrangement and the placing of the second laser line on said received at least one image, and wherein the computation unit further is configured to determine the depth of potential holes (21) or grooves based on the computed distance between the product (20, 21) and the first camera arrangement (31) at many points.

16. The arrangement according to claim 7, further comprising at least one second illumination arrangement (32, 33), wherein the computation unit further is configured to identify damages on the surface of the product based on said at least one image.

17. A method (400) for controlling a product which is transported with the help of a transport arrangement during or after the production process, wherein the method comprises the steps of: emitting first light (410) to the product from at least a first side in such a way that a part of the first light reaches the product and the other part of the first light is retro-reflected from a surface which is situated on the opposite side of the product; detecting a first image (420) of the product on the same side of the product from which the first light is emitted in such a way that the angle of incidence from the illumination is substantially the same or the same as the angle of observation for each point in the image plane; extracting edge information (430) from the first detected image; determining at least one of the form, a position, or an orientation (440) of the product in the image based on the extracted edge information; additionally illuminating the product (510) from one or several angles that don't differ with more than 90 degrees from the direction from which the first light is emitted; detecting (520) in an image the light from the additional illumination which has been reflected there from the product; and determining (530) whether the hole and/or groove configuration of the product is in agreement with a specification of the product based on the detected image.

18. The method according to claim 17, further comprising the step of determining whether the geometry of the product is in agreement with a pre-defined specification of the product (450) based on the determined form and/or position and/or orientation.

19. The method according to claim 18, wherein the geometry of the product comprises at least some of the width, length, rectangularness, and/or other two-dimensional geometrical form of the product.

20. The method according to claim 17, wherein the hole and/or groove configuration of the product comprises at least some out of presence, position, or size of the holes and/or grooves.

21. The method according to claim 17, further comprising the steps of:
projecting at least one laser line basically crosswise to the moving direction of the product;
detecting said projected at least one laser line in an image, which corresponds to the first image;
determining a distance between an image detection element and the product based on the detected image and triangulation; and
using the determined distance for determining the form and/or hole and/or groove configuration of the product.

22. The method according to claim 17, further comprising the steps of:
projecting a pattern having a plurality of points on the product, via a laser projection;
detecting at least a part of said projected pattern on an image, which corresponds to the first image;
determining a plurality of distances between an image detecting element and respective point out of the pattern which is projected on the product based on the detected image and triangulation; and
determining whether the product is bent and/or turned based on said plurality of determined distances, and/or determining the height position of the product based on said plurality of determined distances.

23. The method according to claim 17, further comprising the steps of: projecting a laser line basically crosswise to the moving direction of the product; detecting the projected laser line on an image, which corresponds to the first image; determining distance between an image detection element and several points along the projected laser line based on the detected image and triangulation; and using the determined distances for determining whether the depth of the hole/-s and/or the groove/-s of the product is in agreement with a specification of the product.

24. A computer program product comprising at least one non-transitory computer-readable storage medium having computer-readable program code portions embodied therein, the computer-readable program code portions comprising at least one executable portion configured for: emitting first light (410) to the product from at least a first side in such a way that a part of the first light reaches the product and the other part of the first light is retro-reflected from a surface which is situated on the opposite side of the product; detecting a first image (420) of the product on the same side of the product from which the first light is emitted in such a way that the angle of incidence from the illumination is substantially the same or the same as the angle of observation for each point in the image plane; extracting edge information (430) from the first detected image; determining at least one of the form, a position, or an orientation (440) of the product in the image based on the extracted edge information additionally illuminating the product (510) from one or several angles that don't differ with more than 90 degrees from the direction from which the first light is emitted; detecting (520) in an image the light from the additional illumination which has been reflected there from the product; and determining (530) whether the hole and/or groove configuration of the product is in agreement with a specification of the product based on the detected image.

25. The arrangement according to claim 1, wherein the arrangement is arranged in such a way that the biggest part of the light from said first illumination arrangement (30), which arrives at said first camera arrangement (31), arrives at said first camera arrangement (31) by way of the light being sent there from a side of the product (20, 21) which is opposite the side of the product where the first camera arrangement (31) is situated.

26. The arrangement according to claim 1, wherein the first illumination arrangement (60) is arranged on the side opposite to the first camera arrangement (31), and where the first illumination arrangement (60) comprises a luminous screen (60).

* * * * *